(12) United States Patent
Suzuki

(10) Patent No.: US 6,313,372 B1
(45) Date of Patent: Nov. 6, 2001

(54) STRETCH-ACTIVATED ELASTIC COMPOSITE

(75) Inventor: Migaku Suzuki, Kanagawa (JP)

(73) Assignee: Paragon Trade Brands, Inc., Norcross, GA (US)

(*) Notice: Subject to any disclaimer, the term of this patent is extended or adjusted under 35 U.S.C. 154(b) by 0 days.

(21) Appl. No.: 08/663,300

(22) PCT Filed: Jan. 17, 1995

(86) PCT No.: PCT/US95/00505
§ 371 Date: Jun. 21, 1996
§ 102(e) Date: Jun. 21, 1996

(87) PCT Pub. No.: WO95/19258
PCT Pub. Date: Jul. 20, 1995

(30) Foreign Application Priority Data

Jan. 18, 1994 (JP) ................................... 6-003711

(51) Int. Cl.$^7$ ............................................. A61F 13/15
(52) U.S. Cl. ....................... 604/365; 604/366; 604/372; 604/373; 604/370; 604/385.25; 604/385.29; 604/385.3; 156/183; 156/344; 428/198; 428/221
(58) Field of Search ................ 604/385.1, 385.2, 604/392–396, 365, 366, 370, 385.24–385.3, 372; 428/198, 221, 224; 156/183, 344

(56) References Cited

U.S. PATENT DOCUMENTS

| | | | |
|---|---|---|---|
| 4,205,679 | * | 6/1980 | Repke et al. ........................ 604/385.2 |
| 4,450,026 | * | 5/1984 | Pieniak et al. ..................... 604/385.2 |
| 4,938,757 | * | 7/1990 | Van Gompel et al. .............. 604/396 |

* cited by examiner

*Primary Examiner*—Glenn K. Dawson
*Assistant Examiner*—K. M. Reichie
(74) *Attorney, Agent, or Firm*—Hunton and Williams

(57) ABSTRACT

A stretch-activated elastic composite includes a non-woven fabric having a potential elongatability of higher than 100% in a predetermined direction, and an elastically recoverable, elastic sheet. The elastic sheet in its unstretched state is partially bonded to the non-woven fabric in its unelongated state. The elastic composite exhibits, per unit width of 5 cm, (1) a stress of lower than 1000 g at 30% stretch, (2) a stress of higher than 400 g at 100% stretch, (3) a breaking point of higher than 400 g and (4) an elastic limit of higher than 200%. The elastic composite after being stretched at a rate of lower than 200% exhibits, per unit width of 5 cm, (1) a stress of lower than 500 g at 30% stretch and (2) a stress of higher than 100 g at 100% stretch. The elastic composite after three repeated cycles of 150% stretching and relaxing exhibits an elastic recovery rate of higher than 60%. The elastic composite of the present invention provides excellent performance in elastic recovery, is soft to the touch, and is best utilized in elasticizing an article portion which is brought into direct contact with human skin.

14 Claims, 16 Drawing Sheets

STRETCH-ACTIVATED ELASTIC COMPOSITE

FIELD OF THE INVENTION

The present invention relates to an elastic composite which comprises a non-woven fabric and an elastic sheet, and which exhibits excellent elastic recovery and a soft surface touch. The elastic composite can be advantageously utilized in elasticizing an article which is brought into direct contact with the human skin during use, such as a sleeve of a medical gown, or a waist or crotch portion of a sanitary article.

BACKGROUND OF THE INVENTION

In recent years, disposable articles, including medical and sanitary articles, etc., have widely used elastic material to improve the fit to the human body. Particularly, infant articles utilize an elastic sheet and a non-woven fabric composite much more frequently than an elastic sheet alone. In the elastic sheet and the non-woven fabric composite, the elastic sheet exhibits elastic properties and the non-woven fabric provides improved surface structure and reinforcement of the elastic sheet.

A typical example of such an elastic composite is a three-layer composite called S.M.S. (spunbonded/meltblown/spunbonded) which is disclosed in U.S. Pat. Nos. 4,663,220; 4,652,487; and 4,720,415. This composite is manufactured by a method called S.B.L. (Stretch-Bonded Laminate) wherein the elastic sheet is first stretched and is in its stretched state bonded to the non-woven fabric to form the composite upon release. The composite manufactured in accordance with this method has a stable range of elasticity and neither expands beyond the range nor breaks during normal use since its expansion limit corresponds to its stretched range during manufacture. However, the composite disadvantageously uses more of the non-woven fabric than may be necessary and is bulky so that it is not well-suited for high-speed commercial production.

Japanese Patent No. 4-281059 also discloses a method for directly entangling fibers into an elastic net, which, however, is costly. In order to remedy these drawbacks, an attempt (EPC No. 556,749) has been made to bond an elongatable non-woven fabric to an elastic film on line to form a composite of channel-like construction.

Japanese Utility Model No. 3-39509 discloses an elastic composite which is constructed by hydro-entangling a web comprising staple fibers and a non-woven fabric directly formed of thermoplastic elastomers. In order for the composite to have stretchability of higher than 70%, the web includes fibers which slightly crimp upon application of heat or which split into fibers of finer than 1 denier.

The above conventional composites are capable of expanding over a wide range from a breaking point of the non-woven fabric to a breaking point of the elastic sheet. Their critical points however create difficulty in designing products and defining its specifications. It also leaves users with insufficient knowledge of the proper use since they do not know at what point the composite breaks.

SUMMARY OF THE INVENTION

An object of the present invention is to provide a highly productive, economical and functional elastic composite which utilizes individual properties of a non-woven fabric and an elastic sheet in combination. Another object of the invention is to provide a method for manufacturing such an elastic composite.

In accordance with the embodiments of the present invention, there is provided a stretch-activated elastic composite which comprises a non-woven fabric having a potential elongatability of higher than 100% in a biased direction, an elastic sheet having an elastic recovery rate of higher than 60%, and an elastic limit of higher than 200%. The non-woven fabric in its unelongated state is partially bonded to one surface of the unstretched elastic sheet in securement regions. The elastic composite exhibits, per unit width of 5 cm, (1) a stress of lower than 1000 g at 30% stretch, (2) a stress of higher than 400 g at 100% stretch, (3) a breaking point of higher than 400 g, and (4) an elastic limit of higher than 200%. The elastic composite after being stretched less than 200% exhibits, per unit width of 5 cm, (1) a stress of lower than 500 g at 30% stretch and (2) a stress of higher than 100 g at 100% stretch. The elastic composite after three repeated cycles of 150% stretching and relaxing exhibits an elastic recovery rate of higher than 60%. "Strain" as used herein means the amount of elongation of the material when a stretching force is applied. "Stress" is the force applied to produce the strain.

In order to optimize the elastic composite structure in accordance with the preferred embodiments of the present invention, it becomes important to combine respective characteristics of the non-woven fabric and the elastic sheet thereby improving their functions synergistically. Since the elastic sheet may be expensive relative to the non-woven fabric, the addition of the non-woven fabric thereto further improves the cost/performance ratio of the elastic composite.

In accordance with the present invention, the designs of the expandable non-woven fabric and selections of the bonding method provide a wide range of selection of the elastic sheet and permit the elastic sheet to fully exhibit its desired functionality.

(1) The expandability of the non-woven fabric enables the elastic composite, which is not elastically stretchable in a normal condition, to have the property that it is activated by expansion to become elastically stretchable and contractable.

(2) With a suitable selection of its entanglement condition an expandable, hydro-entangled non-woven fabric enables the resulting non-woven fabric to have good expandability as well as two-phase expandability which creates a second increase in stress beyond a first stress point.

(3) Securement regions for securing the elastic sheet to the non-woven fabric are provided to extend transversely of the expandable direction of the elastic composite so that the securement regions provide less resistance to the expandability of the elastic composite.

(4) The securement regions provided between the non-woven fabric and a top surface of the elastic sheet are staggered from the securement regions provided between the non-woven fabric and a bottom surface of the elastic sheet to prevent the top and bottom securement regions from overlapping. This prevents brittleness. Where heat bonding is used, some brittleness may occur where the heat is applied. By staggering, as described, such brittleness (which may be undesirable) does not extend through the composite.

The above considerations in designing the elastic composite enable production of an elastically recoverable elastic composite which has excellent expandability under low strain.

The present invention further provides a method for manufacturing an elastic composite having the above-described characteristics. This method will now be explained in detail with reference to the accompanying drawings.

DETAILED DESCRIPTION OF PREFERRED EMBODIMENTS

Figure 1:
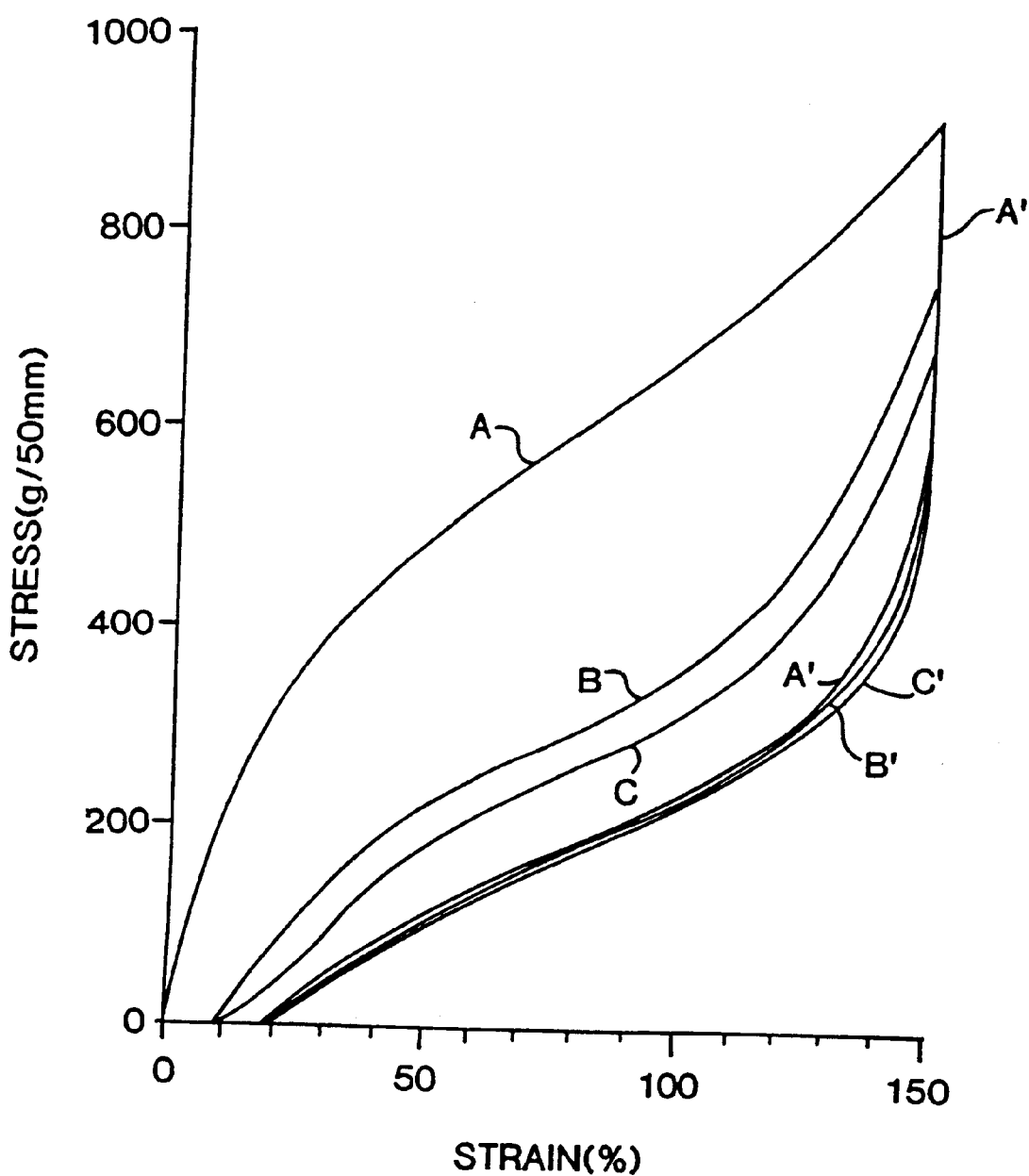
FIG. 1 is a graph showing S-S (stress-strain) curves of an elastic composite in accordance with the present invention.
Figure 2:
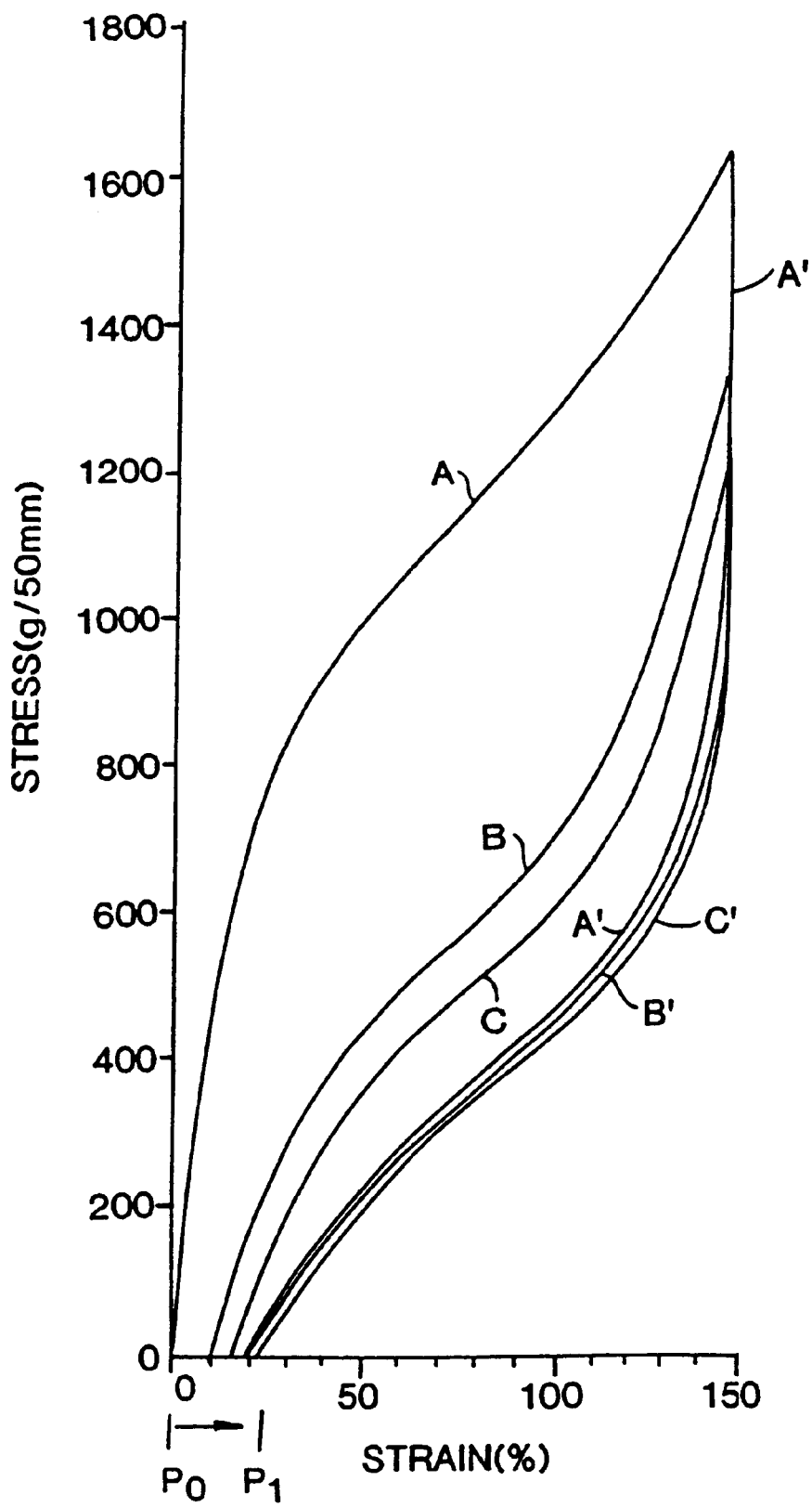
FIG. 2 is a graph showing S-S curves of another elastic composite in accordance with the present invention.
Figure 3:
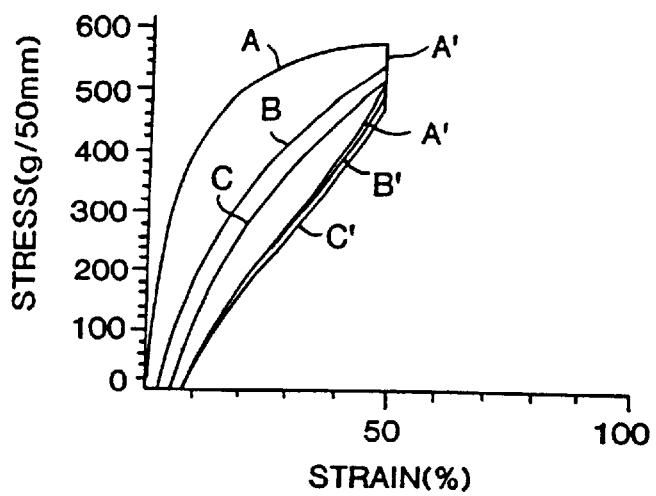
FIG. 3 is a graph showing S-S curves of the elastic composite when stretched at a selected rate and released.
Figure 4:
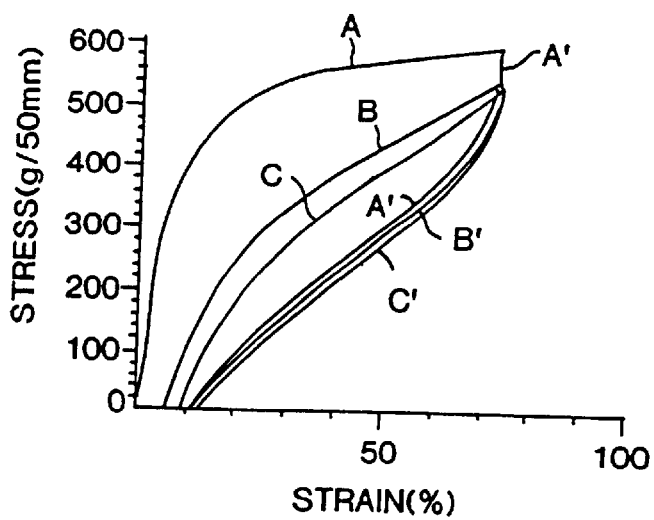
FIG. 4 is a graph showing S-S curves of the elastic composite when stretched at a rate different from that of FIG. 3 and released.
Figure 5:
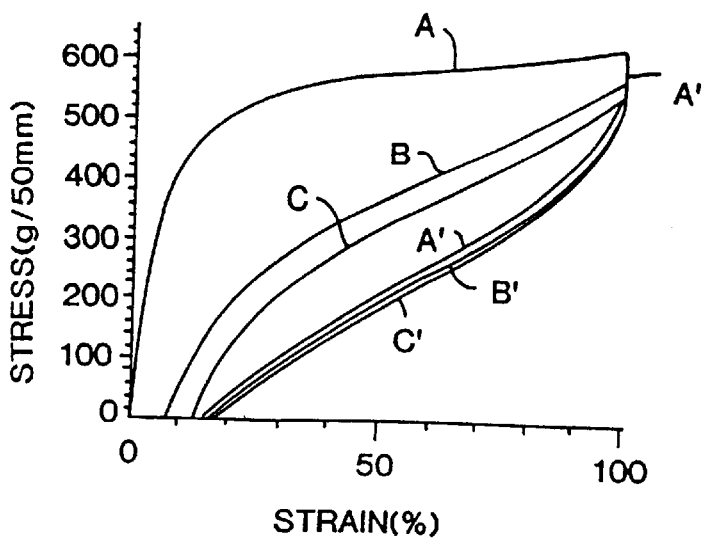
FIG. 5 is a graph showing S-S curves of the elastic composite when stretched at a rate different from that of FIG. 3 and released.
Figure 6:
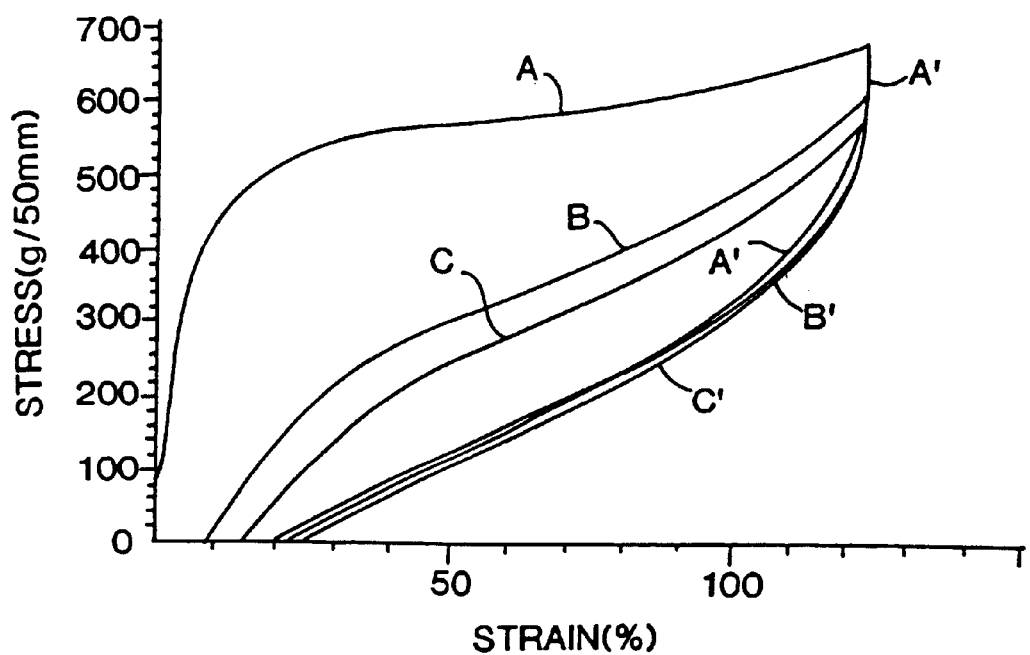
FIG. 6 is a graph showing S-S curves of the elastic composite when stretched at a rate different from that of FIG. 3 and released.

First, an explanation of stretch-activation is in order. FIGS. 1 and 2 show typical S-S strain-stress) curves of elastic composites in accordance with the present invention. Initial stretch of the elastic composite causes the elastic sheet and the non-woven fabric to experience structural changes concurrently. The elastic composite initially shows a relatively high stress. Once the elastic composite is initially stretched, the non-woven fabric has already elongated and exhibits less resistance to a second stretch. The elastic composite subsequently exhibits the elastic characteristics of the elastic sheet at a second stretch, and similarly at a third stretch and stretches thereafter. The appearance of such a phenomenon will be referred to as stretch-activation in this specification.

Figure 7:
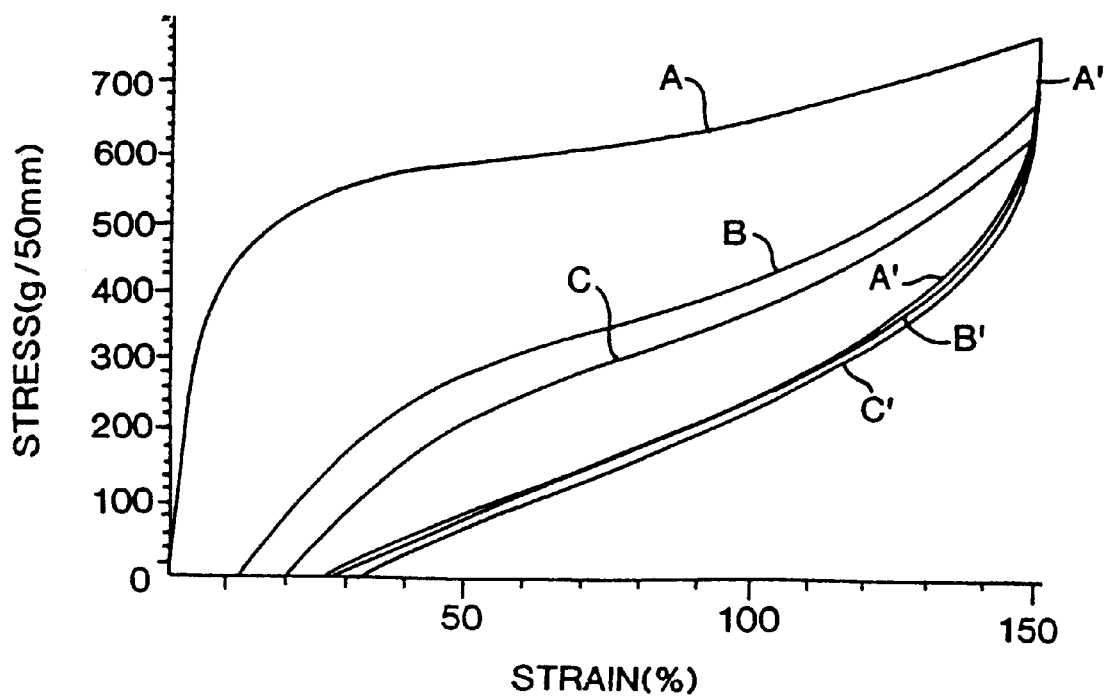
FIG. 7 is a graph showing S-S curves of the elastic composite when stretched at a rate different from that of FIG. 3 and released.

Another important feature of the stretch-activation is that the elastic composite exhibits its elasticity within ranges depending upon stretching rates, as illustrated in FIGS. 3 through 7. FIGS. 3–7, respectively, show S-S curves for an elastic composite similar to that depicted in FIG. 1, but with the maximum strain depicted being 50% (FIG. 3); 75% (FIG. 4); 100% (FIG. 5); 125% (FIG. 6) and 150% (FIG. 7). Accordingly, when the elastic composite is applied to a user's body, it elastically stretches and contracts within a range corresponding to movements of the user's body so that a flexible and efficient, fitting structure can be provided.

The stretch-activation, in some cases, might occur automatically when the elastic composite attached to a final product is stretched upon wearing. However, it may be desirable that such stretch-activation be done either prior to or during the production of a product using the composite. For instance, in an absorbent product using the elastic composite for a waist gather, the following two cases can be considered: (1) a previously stretch-activated elastic composite is used; or (2) stretch-activation of the elastic composite is done during the production process. In the former case, the material is bulky. In the latter case, bulkiness will be less of a problem. During the production of a product using the elastic composite which has not been previously stretch-activated, a roll having deep corrugations or grooves in its peripheral surface may be used in the production line for achieving partial stretch in the elastic composite. In such a case, careful attention is required to prevent damage to the surfaces of the non-woven fabric and elastic sheet.

Such a stretch-activated elastic composite preferably shows low stress and a rapid increase in resistance as it exceeds a certain range of stretching rate so that it stops stretching before it breaks. In other words, such composite shows low resistance to stretching in the activated range but at the upper stretching limit it shows a rapid increase in resistance to stretching.

It is further important that the elastic composite maintains its elastic characteristics even after being stretched and released repeatedly. The important and basic characteristic of the elastic composite accordingly resides in its low residual strain.

The characteristics of a preferred embodiment of the elastic composite of the invention will now be described.

The following results of measurements for physical characteristics were done according to methods commonly used in this field of industry and based on the JIS (Japanese Industrial Standards) standards. Major points of the measurements are given below:

(1) Samples to be tested
   Width: 5 cm
   Length: 15 cm
(2) Measurement condition for S-S curves
   Chuck distance: 10 cm
   Loading speed: 20 cm/min.
(3) Cycle tests Loading and unloading cycles are repeated three times at 150% stretch and hysteresis curves are obtained. Stress values are read at 30% and 100% from the final returning point of the hysteresis curves. Between the cycles, an ease time in which all loading is released, is given as shown below:

$1^{st}$ Measurement—first 5 minute ease time—$2^{nd}$ Measurement—second 5 minute ease time—$3^{rd}$ Measurement—third 5 minute ease time. The hysteresis curves as shown in FIGS. 1 and 2 correspond to this cycle. Line A below shows the first loading cycle. Line A' shows the recovery during the first ease time. Line B shows the second loading cycle. Line B' shows the recovery during the second ease time. Line C shows the third loading cycle. Line C' shows the recovery during the third ease time.

An elastic composite 5 cm wide is sampled to measure an S-S curve during its first cycle of stretch and release, showing the following desirable characteristics:

(1) Stress at 30% stretch

This shows the initial stress against stretch, which corresponds to the first expansion upon using. A 30% stretch is selected as an indicator, showing the initial stretch modulus, since it is commonly used in the fiber industry. This value should be selected carefully because too large an initial stress will create too tight a feeling. It has been found through experience, a desirable value is not more than 1,000 g, preferably 800 g and more preferably 600 g.

(2) Stress at 100% stretch

This is the stress necessary for stretch-activation, but may vary with usage or with the maximum degree of stretch upon using. In general, the elastic composite of the present invention displays its characteristics at a highly stretched condition and will usually be used over 100% stretch, so that a stress at 100% stretch is selected for an evaluation point.

The elastic composite of this invention should have 400 g or more stress at 100% stretch, preferably 600 g, and more preferably 800 g stretch, thereby achieving desirable stretch-activation.

(3) Stress at a breaking point

A sufficient stress is usually 400 g or more. However, accidental breaking is less common when the stress is higher than 600 g, because one can more easily feel the resistance as the composite approaches the limit of stretch.

Such an elastic composite will have a very low measured stress value after stretch-activation. For example, after being stretch-activated at 150% stretch, the value when the composite is stretched less than 150% will be significantly decreased. Such decrease in stress is desirable in view of the objectives of the usage of the composite of the present invention.

Desirable S-S properties of an elastic composite of the present invention at 150% stretch are as follows:

(1) Stress at 30% stretch

The stress should be less than 500 g, preferably less than 400 g, and more preferably less than 300 g following stretch-activation. By selecting such stress levels, potentially uncomfortably high compression on the body can be avoided when the elastic composite is used, for example, in products for infants.

(2) Stress at 100% stretch

After stretch-activation, the stress at 100% stretch will become significantly lower, while providing a suitable stretch resistance to provide a secure fit to the wearer. The minimum stress is higher than 100 g, preferably higher than 200 g.

A second S-S curve measurement shows the following characteristics:

(1) Stress at 30% stretch

Considering its conformability to a user, the stress is preferably less than 500 g, and more preferably less than 400 g.

(2) Stress at 100% stretch

The stress decreases by over 100 g, compared to the first measurement.

It is further important that the elastic composite exhibits a high elastic recovery rate, and accordingly a low residual strain. In evaluating its performance in elastic recovery, the elastic recovery rate generally is measured after three repeated cycles of stretching 150% and then releasing the composite. The elastic recovery ratio is determined by comparing the returning point (P1), such as shown in FIG. 2, against the staring point (P0) against the whole elastic ratio. For example, assuming point P1 is at 30% for an elastic ratio of 100%, the recovery ratio is calculated by the following formula:

$$\text{Recovery Ratio} = 100 - P1 - P0/150 \times 100 = 100 - (30/150 \times 100) = 80(\%)$$

The desirable elastic recovery rate is higher than 60%, and preferably higher than 70%. Constituent elements of the elastic composite having such elastic recovery will now be explained.

The elastic sheet to be used preferably is selected from materials having stretchability of higher than 20% and elastic recovery of higher than 60%. Materials having such characteristics include foams such as of urethanes or rubber latexes; synthetic rubber films such as of isoprenes or butadienes; styrene-type elastomer films such as of SIS (stylene isoprene stylene), SEBS (stylene ethylene butadiene stylene), and SEPS (stylene ethylene propylene stylene); polyolefin elastomer films such as of EVA (ethyl vinyl acetate), EMA (ethyl methyl acrylate), and EPDM (ethylene propylene diene terpolymer); and meltblown elastomer non-wovens such as polyurethane, SIS (stylene ispreren stylene) and SEBS. The elastic sheet more preferably comprises a film, net-like formation, or meltblown non-woven, formed of heat-sealable styrene-type elastomers such as SIS or SEBS, or blends thereof.

The constituent element of the elastic composite of the present invention, the non-woven, will now be explained.

The most suitable presently known non-woven fabric for use in the present invention is a hydro-entangled or spun-laced non-woven fabric, preferably having high elongatability in the machine direction (MD) or in the cross-direction (CD). The non-woven fabric having high CD-elongatability can be obtained by hydro-entangling a longitudinally oriented, parallel carded web which has a high MD/CD ratio, i.e., the fibers extend predominantly in the machine direction. The non-woven fabric having high elongatability in the MD can be obtained by hydro-entangling a randomly oriented fibrous web comprising highly shrinkable fibers, overfeeding the entangled web in the MD and drying before it is treated to shrink.

Such MD-elongatability or CD-elongatability is preferably higher than 100%, and more preferably higher than 200%.

The elongatability of the non-woven fabric allows the non-woven fabric to follow the action of the elastic sheet when they are combined with each other.

The non-woven fabric has another important characteristic as well as its elongatability.

As the elongation of the non-woven fabric exceeds a certain extent, the non-woven fabric starts showing resistance to further elongation.

Figure 8:
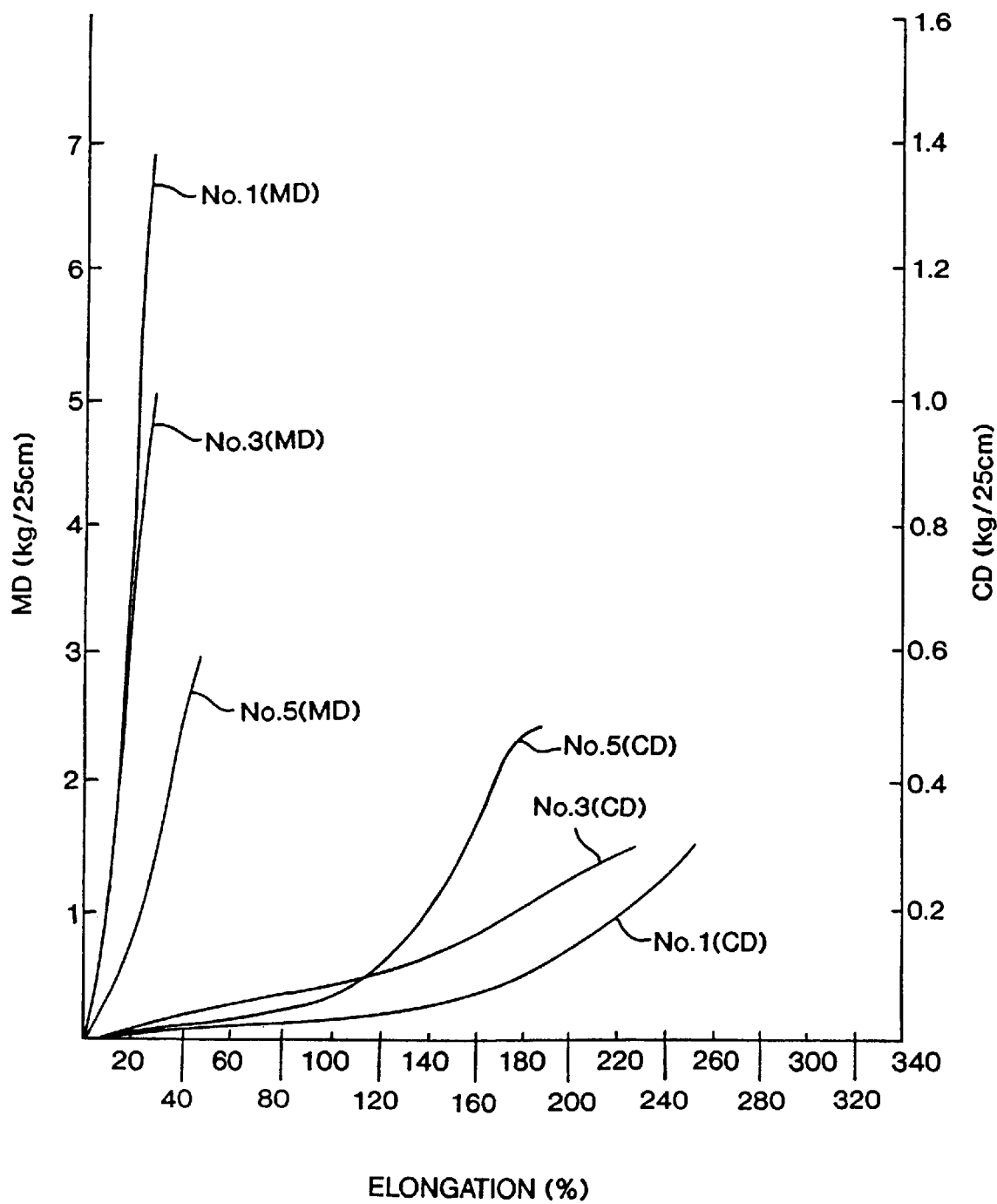
FIG. 8 is a graph showing S-S curves of three different non-woven fabrics hydro-entangled by regular means when they are stretched both in the MD (machine direction) and in the CD (cross direction).

For comparison, FIG. 8 shows exemplary CD and MD Stress-Strain (S-S) curves of three different non-woven fabrics designated Nos. 1, 3 and 5 which are respectively prepared by hydro-entangling normal parallel webs by conventional means. As apparent from FIG. 8, these non-woven fabrics are highly elongatable in the CD. No resistance appears when each of the non-woven fabrics exceeds its elastic limit before it finally breaks.

Figure 9:
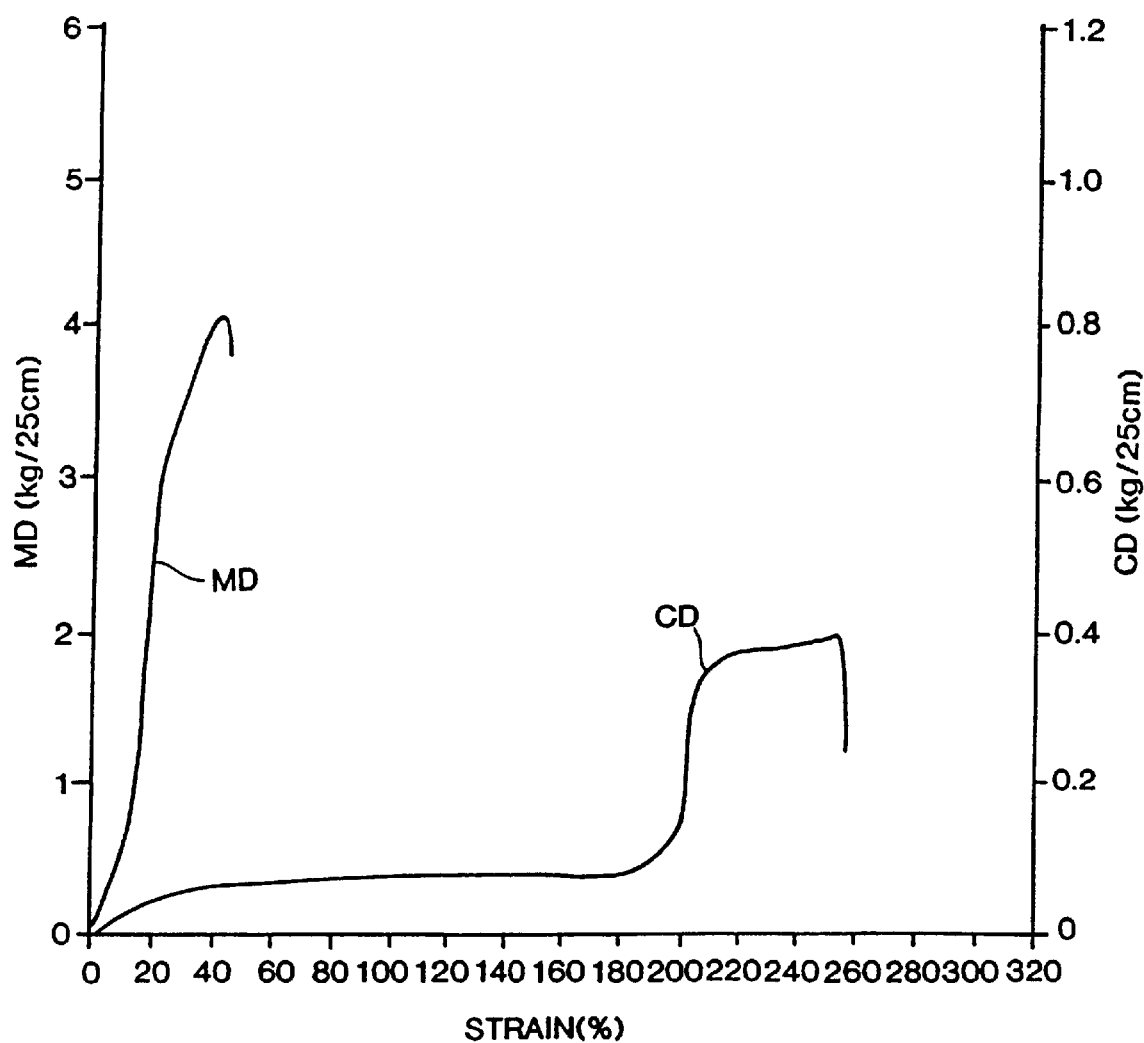
FIG. 9 is a graph showing S-S curves of the non-woven fabric used in the present invention when stretched both in the MD and in the CD.

In contrast, a spunlaced non-woven fabric (which also may be known as a "hydro-entangled non-woven" or a "water jet entangled non-woven") shows rapid increase in stress at about 200% stretch as illustrated in FIG. 9. With the stress maintained, the non-woven fabric continues to elongate until it breaks at a breaking point (about 260% stretch). This second-phase increase in stress at about 200% stress acts to resist breaking before the non-woven fabric finally breaks. It is desirable to select physical properties of the non-woven fabric so that the second-phase increase in stress takes place preferably at higher than 150% stretch, and more preferably at higher than 200% stretch.

In order for the non-woven fabric to exhibit such characteristics, the fibrous web construction and the condition for hydro-entanglement thereof need to be selectively combined.

For example, the following non-woven fabric meets such requirements.

(1) Web construction

Relatively short staple fibers of 25–45 mm long are mixed with relatively long staple fibers of 45–60 mm long to prepare raw staple fibers.

Fibers are further mixed therein which are capable of shrinking to crimp.

(2) Selection of condition for hydro-entanglement

Hydro-jets from fine nozzles integrally entangle fibers in the web over its whole area, and thereafter intensely hydro-entangle the web at transverse intervals. For example, three parallel rows of the nozzles are disposed to hydro-entangle the fibers in three stages:

| First stage:  | nozzle diameter: | 0.15 mm φ |
|---|---|---|
|   | nozzle pitch:    | 0.5 mm    |
|   | water pressure:  | 30 kg/cm² |
| Second stage: | nozzle diameter: | 0.15 mm φ |
|   | nozzle pitch:    | 0.5 mm    |
|   | water pressure:  | 50 kg/cm² |
| Third stage:  | nozzle diameter: | 0.20 mm φ |
|   | nozzle pitch:    | 1.0 mm    |
|   | water pressure:  | 60 kg/cm² |

A spun-laced non-woven fabric having a striped pattern is obtained under the above conditions.

The elastic composite of the present invention comprises an elongatable non-woven fabric bonded to a top surface or to the top and bottom surfaces of the elastic sheet. Although the bonding method is not specifically limited, different bonding methods may cause the resultant elastic composite to have different characteristics. Regardless of the selected bonding method, the following factors become important:

(1) The non-woven fabric is bonded to the elastic sheet so that the readily elongatable direction of the non-woven fabric is brought into agreement with the readily stretchable direction of the elastic sheet.

(2) The bonding is made to form securement regions in a selected pattern so that it does not disturb effective elongation of the non-woven fabric and effective stretching of the elastic sheet. To this end, it is desirable that the securement regions are arranged to define as small in number and area as possible in the readily elongatable direction. Such bonding can be easily made by distributing securement regions, preferably in the range of 90° (+10°), with respect to the readily elongatable direction of the non-woven fabric.

Figure 10A:
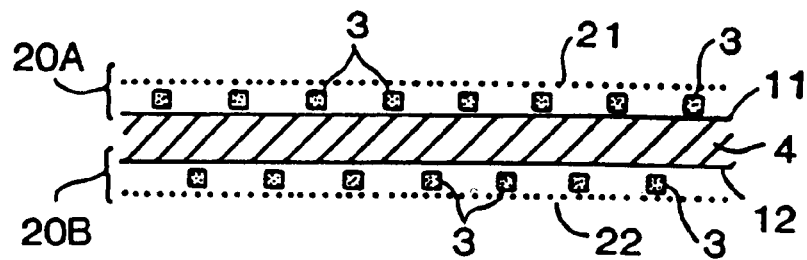
FIGS. 10A, 10B and 10C are schematic cross-sectional views respectively illustrating exemplary arrangements of the elastic sheet and the non-woven fabric in accordance with the present invention.
Figure 10B:
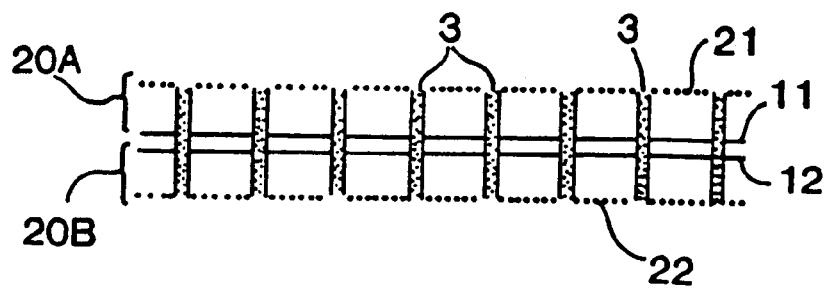
Figure 10C:
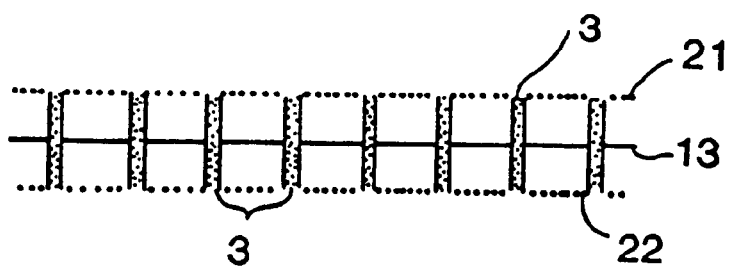

(3) When non-woven fabric is placed on opposite surfaces of the elastic sheet, the placement of the securement regions respectively between the one non-woven fabric and the elastic sheet and between the other non-woven fabric and the elastic sheet greatly affect the elastic characteristics of the formed elastic composite. In an elastic composite having an elastic sheet positioned between two non-woven fabrics, the elastic sheet may comprise one sheet of an elastic film of 50 μm thick or two sheets of an elastic film of 25 μm, supposing that the desirable thickness of the elastic sheet is selected to be 50 μm. However, it should be recognized that 50 μm is used as an example and other thicknesses may be used as well. FIGS. 10A, 10B and 10C illustrate three typical alternative embodiments for combining the elastic sheet and the non-woven fabric.

In FIG. 10A two elastic sheets 11, 12 each having a thickness of 25 μm are bonded at securement regions 3 to two non-woven fabric sheets 21, 22, respectively to form two elastic composites 20A, 20B which are bonded to each other by hot pressing as in region 4.

In FIG. 10B two elastic sheets 11, 12 each having a thickness of 25 μm are placed and bonded between two non-woven fabrics 21, 22 through securement regions 3 such as by hot pressing.

In FIG. 10C an elastic sheet 13 of 50 μm thick is positioned between two non-woven fabric sheets 21, 22 and bonded thereto at securement regions 3.

An S-S curve is measured for each construction illustrated in FIGS. 10A, 10B and 10C. Each construction is stretched by 100% and subsequently released to compare its length with its initial length prior to stretching. Better elastic recoveries are observed in 10B than 10C, and in 10A than 10B, respectively.

In FIG. 10A, the securement regions 3 of the elastic sheet 11 and the non-woven fabric 21 are staggered from the securement regions 3 of the elastic sheet 12 and the non-woven fabric 22. The securement regions 3 upon which tensile stress is concentrated are arranged in different locations between the top and the bottom of the elastic composite so that the formed elastic composite has a relatively high tensile strength.

The industrial process for combining two sheets of a relatively thin one-sided composite to form a two-sided composite also improves production efficiency. Especially when polystyrene-type elastomer films such as SIS or SEBS are used for the elastic sheet, the stable two-sided composite can be readily manufactured by simply placing the film surfaces of the two composites onto each other and hot-pressing them since those films are highly heat-bondable. This greatly improves productivity and cost-savings.

Both elastic composites have the non-woven fabric securely placed upon one surface thereof. As illustrated in FIGS. 10A, 10B and 10C, securement regions 3 respectively extend in a band-like manner transversely to, and preferably at angles of 90° (+10°), with respect to the readily elongatable and stretchable direction of the non-woven fabric and the elastic sheet.

The band-like securement regions may secure the non-woven fabric and the elastic sheet entirely over a specified area. Alternatively, the band-like securement regions may comprise a plurality of securement segments arranged in a row toward a selected direction, such as a plurality of dots or line segments distributed in a desirable patterned manner over the specified area.

Figure 11A:
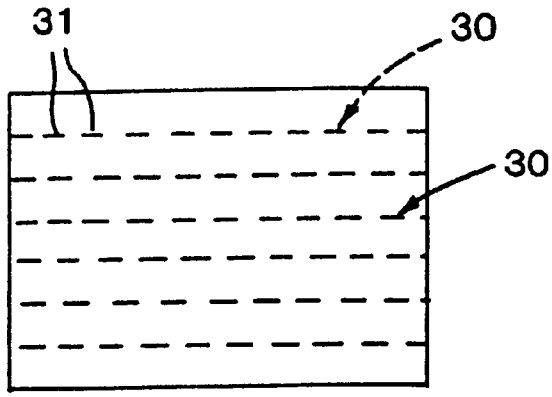
FIGS. 11A, 11B and 11C are representative plan views illustrating exemplary patterned provisions of intermittent securement regions in the elastic composite of the present invention.
Figure 11B:
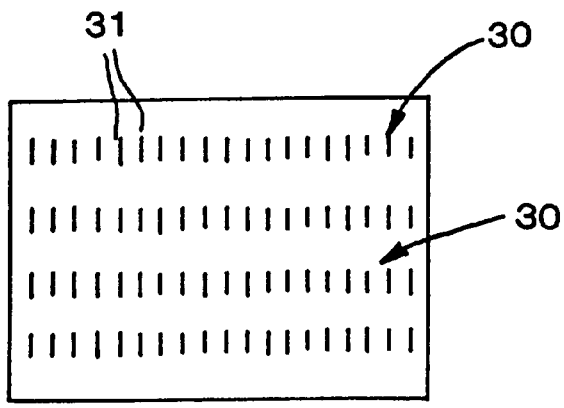
Figure 11C:
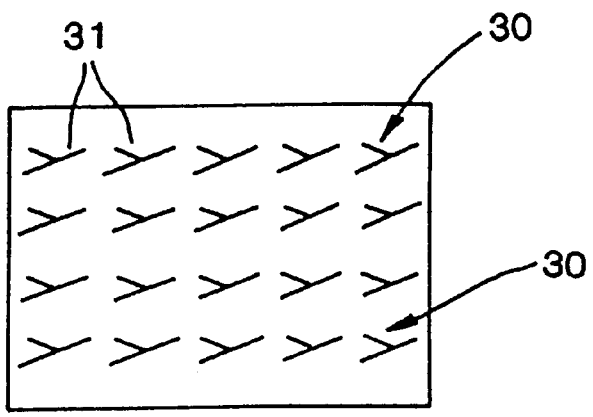

FIG. 11A, 11B and 11C illustrate typical examples of the patterned securement segments arranged at intervals. In FIG. 11A, each of the securement segments 31 comprises a relatively short line segment. The securement segments 31 are arranged at suitable intervals in rows extending in a direction substantially transversely to the readily stretchable direction of the elastic composite to define a plurality of rows 30 of securement segments extending in parallel to each other. In FIG. 11B, each securement segment 31 comprises a line segment and extends substantially transversely to a longitudinal direction of the row 30 of securement segments. In FIG. 11C, each securement segment 31 is substantially Y-shaped, although it may have any selected shape as well as the illustrated shapes.

The elastic composite sacrifices the inherent expansibilities of these materials in the securement regions which secure the non-woven fabric to the elastic sheet so that it is rendered substantially inelastic in the securement regions. Accordingly, when the provisions of the rows 30 of securement segments are made to extend substantially transversely to the readily-stretchable direction as illustrated in FIGS. 11A, 11B, and 11C, such provisions greatly reduce the stretchability of the elastic composite in the direction parallel to the readily stretchable direction even if the materials themselves are highly stretchable in such direction. Substantially, the elastic composite constructions as illustrated in FIG. 11 expand to a very slight extent in the longitudinal direction of the rows 30 of securement segments.

The elastic composite exhibits greatly reduced stretchability in the securement regions even when the non-woven fabric and the elastic sheet are combined by hydroentanglement to provide such securement regions. In contrast to the elastic composite as described in Japanese Utility Model No. 3-39509, the elastic composite of the present invention stretches very slightly in the regions where the non-woven fabric and the elastic sheet are tightly hydroentangled.

However, the elastic composite expands freely in the readily expandable direction transversely to the rows 30 of securement segments until it reaches the elastic limit of the non-woven fabric. The elastic composite returns to its initial length when the tension is released prior to reaching the upper limit. On the other hand, as the elastic composite is further stretched beyond the elastic limit, the non-woven fabric undergoes permanent elongation and never returns to its initial length even after release of the tension. The elastic sheet sustains its elasticity because its elastic limit is much higher than that of the non-woven fabric, and returns to its initial length after release of the tension. When the elastic composite returns to its initial length upon release, the non-woven fabric becomes pouched between the neighboring rows of securement segments.

Once the non-woven fabric undergoes permanent elongation, a smaller force is thereafter required to stretch the elastic composite in the readily stretchable direction than is required when it is initially stretched beyond the elastic limit of the non-woven fabric. This phenomenon typically defines the stretch-activation as mentioned above.

As will be appreciated from the above description, the elastic composite is more resistant to stretching in the direction that the securement regions extend than in the readily stretchable direction thereof The securement segments permit the elastic composite to have its stretchability generally tailored in a desirable and specified direction.

Figure 12A:
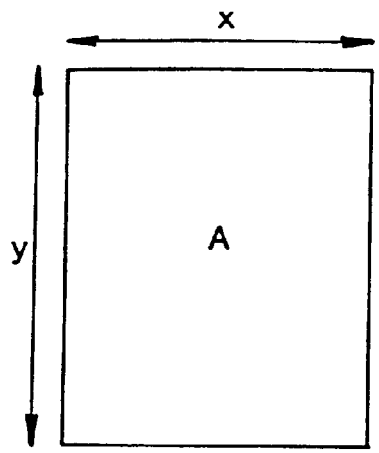
FIGS. 12A, 12B and 12C are representative plan views illustrating exemplary arrangements of intermittent securement regions in the elastic composite of the present invention.
Figure 12B:
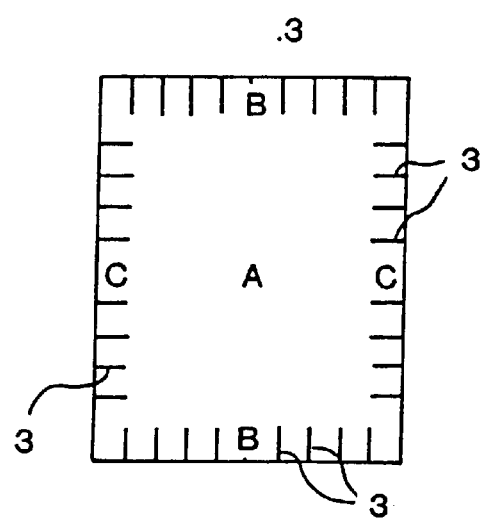

FIG. 12A shows a substantially rectangular elastic composite comprising an elastic sheet and a non-woven fabric which are highly stretchable in both the x and y directions, respectively. As illustrated in FIG. 12B, the elastic composite includes peripheral areas B, C of suitable widths respectively extending along its four linear edges to enclose a central area A. Each of the peripheral areas has linear securement regions 3 which extend transversely to and inwardly from their respective linear periphery. The illustrated elastic composite is stretchable in any direction in the central area A, only in the x direction in the peripheral areas B, and only in the y direction in the peripheral areas C.

Figure 12C:
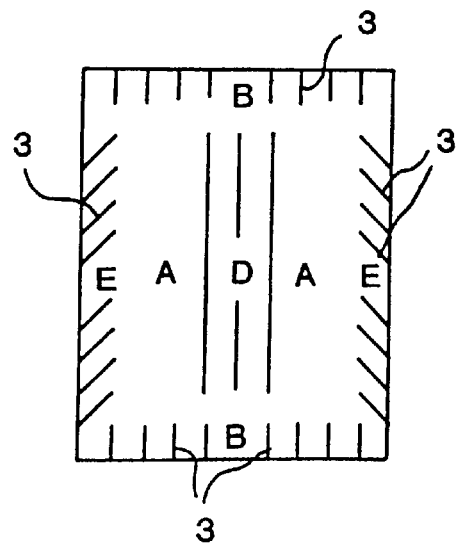

FIG. 12C shows an elastic composite which includes end areas B extending along opposite ends of the elastic composite and an area D extending in the y direction along the composite centerline. Those areas have respective linear securement regions 3 extending in the y direction. The elastic composite further includes end areas E extending along opposite ends thereof. The end areas E have linear securement regions 3 which extend at an angle of about 45° from the respective linear peripheries. Accordingly, the elastic composite is highly stretchable in the x-direction in its areas B and D, and is stretchable in a slanting direction in the end areas E, normal to securement regions 3 in areas E.

Because the elastic composites of FIG. 12B or FIG. 12C have selected areas stretchable only in the respectively specified directions, they can be advantageously used for an elastic topsheet or backsheet of a disposable diaper. In such an event, the end areas B, the end areas C, E and the central area A may serve as waist elastics, leg elastics and expansive elastics for elastically contracting and stretching over an area of the diaper. This enables one to selectively design desirable products which are capable of following any configuration.

Figure 13:
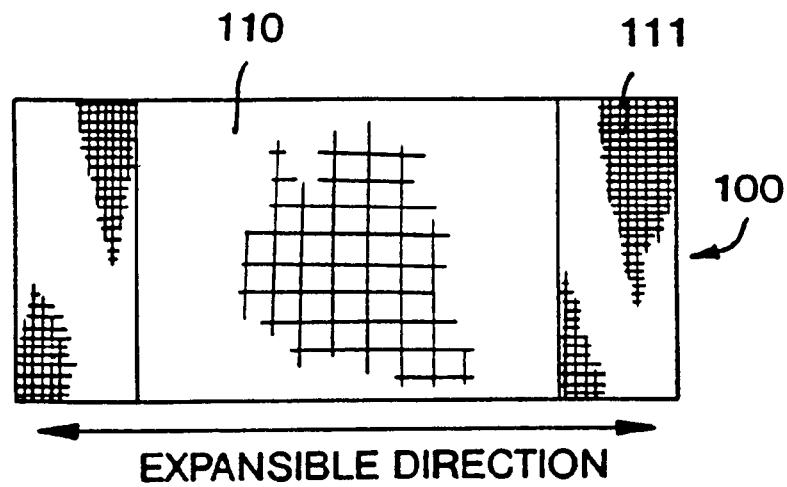
FIG. 13 is a plan view illustrating an exemplary arrangement of intermittent securement regions in the elastic composite of the present invention.

FIG. 13 shows still another elastic composite embodiment of the present invention. An plastic composite 100 is stretchable in only one direction. The elastic composite is highly stretchable in its first central area 110 and is less stretchable or only slightly stretchable in its second opposite end areas 111. The elastic composite with such characteristics can be obtained by applying further bonding treatment such as partially heat-compression treatment to the elastic composite as prepared in the above-mentioned manner.

Figure 14:
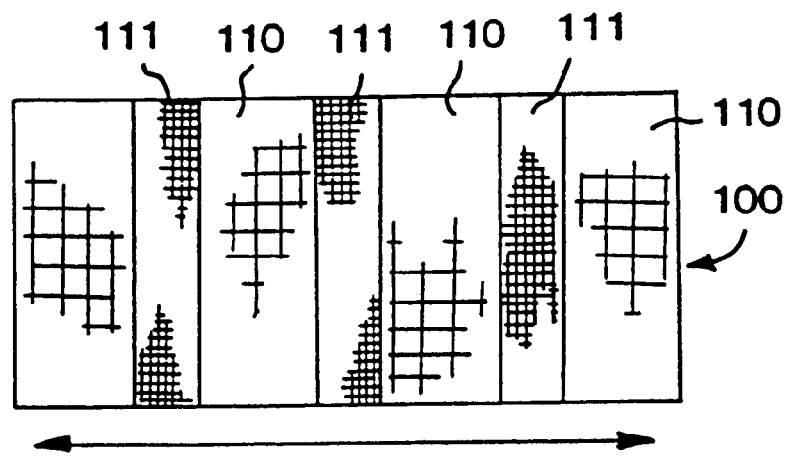
FIG. 14 is a plan view illustrating another exemplary arrangement of intermittent securement regions in the elastic composite of the present invention.

In FIG. 14, an elastic composite has three slightly-stretchable band-like areas 111 disposed at regular intervals.

Figure 15:
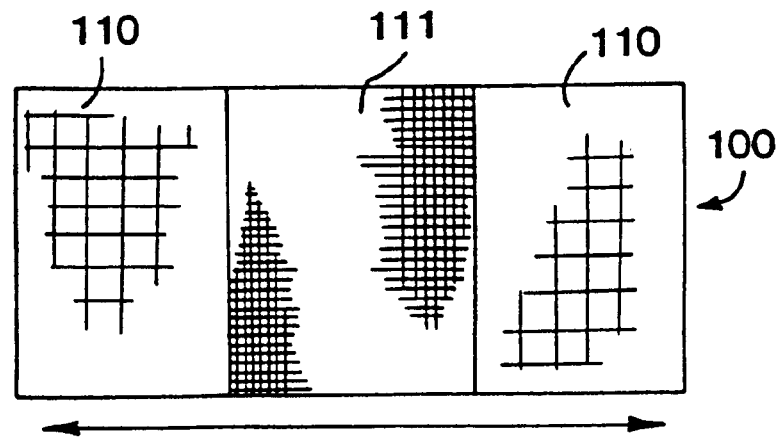
FIG. 15 is a plan view illustrating still another exemplary arrangement of an intermittent securement region in the elastic composite of the present invention.

An elastic composite of FIG. 15 has highly-stretchable areas 110 on opposite sides of a slightly-stretchable band-like area 111. In these illustrated embodiments, the elastic composites comprise an elastic sheet and a non-woven fabric which are both formed of readily heat-fusible materials.

Examples of non-woven fabrics suitable for such requirement include conjugate fibers consisting of a polyester core covered with polyethylene sheath, which is combined with a film of S.E.B.S. (styrene-ethylene-butadiene-styrene block polymer) as an elastic sheet. This material may be easily ultrasonically or heat sealed, and can be used in a high speed production process.

The elastic composites having a highly-stretchable area 110 and a slightly stretchable area 111 is illustrated in FIGS. 13 and 15 can be obtained by applying heat of a suitable temperature range to the area 111.

Figure 16:
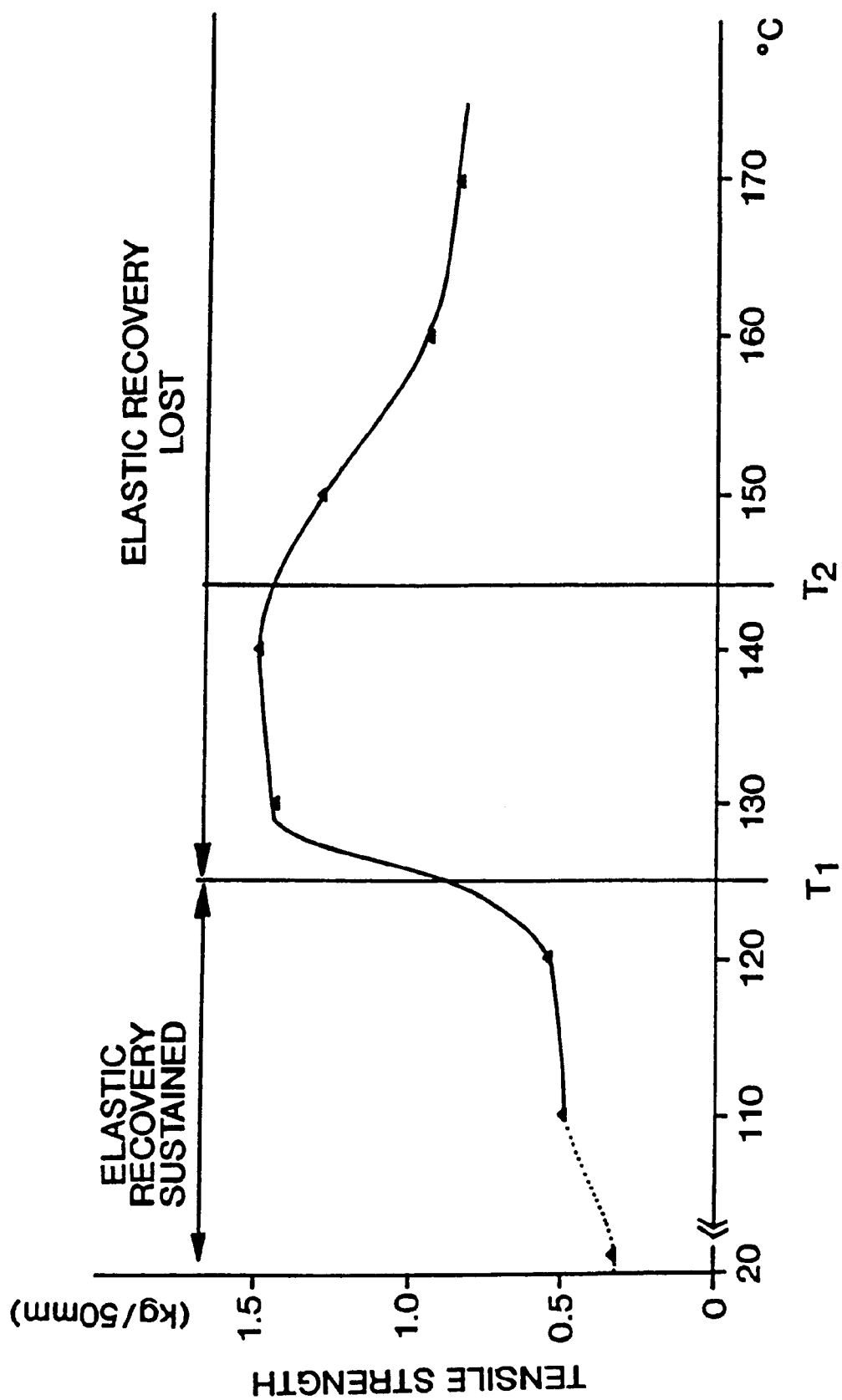
FIG. 16 is a graph of the relationship between tensile strength of the elastic composite and the process temperatures at which the elastic composite is heat-compressed.

FIG. 16 is a graph showing the results measured with regard to a relationship between tensile strength of an elastic composite and temperatures at which the elastic composite is heat-compressed. The elastic composite is prepared by placing an elastic sheet formed of SIS-type film upon a hydro-entangled non-woven fabric comprising PET (polyester) fibers and thereafter partially heat-compressing them for integration. The characteristics of the elastic composite illustrated in FIG. 16 are obtained by further applying heat and compression to the integrated elastic composite.

In the graph, T1 indicates the temperature at which SIS present in the elastic sheet starts to melt and T2 the temperature at which PET present in the non-woven fabric starts to melt, respectively. As can be seen from FIG. 16, heat-compression below T1 is not sufficient to integrate the elastic sheet and the non-woven fabric so that the elastic composite exhibits low tensile strength while sustaining good elastic recovery. When the heat-compression is applied to the elastic composite at a temperature ranging from T1 to T2, at least part of the elastic sheet melts and is fused to the non-woven fabric so that the elastic composite exhibits greatly enhanced tensile strength while recovery is lost. Heat-compression above T2 causes the elastic sheet and the non-woven fabric to be bonded so that the elastic composite exhibits reduced stretchability in all directions.

Referring again to FIGS. 13 and 15, the elastic composites of those characteristics also can be obtained by utilizing different heat-compressive conditions between area 110 and the area 111 when heat-bonding the elastic sheet and the non-woven fabric which are placed upon each other so as to be stretchable in the same direction. Specifically, the elastic sheet and the non-woven fabric are partially heat-compressed in the area 110 at a temperature ranging between T1 and T2 and are entirely heat compressed in the area 111 at a temperature above T1 to render the areas 110 highly-stretchable and the area 111 slightly stretchable. Accordingly, the desirable stretchability can be given to the elastic composite in such a manner. Because the stretchability of the highly-stretchable area 110 is restrained by slightly-stretchable area 111, the elastic composite is characteristically highly stretchable in a specified direction and is slightly stretchable in other directions.

Such elastic composites have highly stretchable and slightly-stretchable areas disposed in a mixed and patterned manner can be applied to various uses. For example, the elastic composite having the slightly-stretchable areas 111 disposed on opposite sides of the highly-stretchable area 110 such as illustrated in FIG. 13 can be applied to tapeless (pant-type) absorbent articles.

Figure 17:
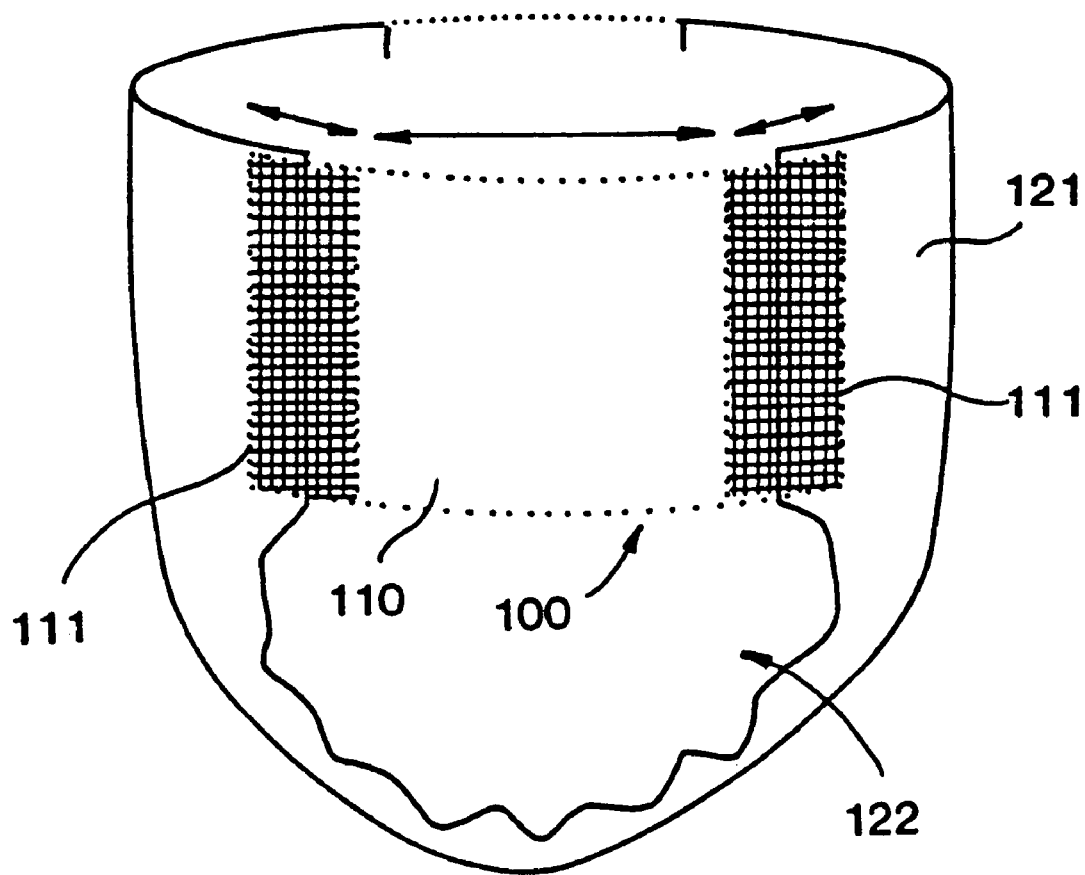
FIG. 17 is a perspective view illustrating an absorbent article which incorporates the elastic composite of FIG. 13 as its side panel.

FIG. 17 illustrates an absorbent article, such as a tapeless diaper, of training pant, having a main body 121 comprising an absorbent body interposed between a liquid permeable topsheet and a liquid impermeable backsheet. The main body is bent along its center line to define a substantially U-shaped configuration. An elastic composite 100 connects opposite side edges of the U-shaped main body to define a leg hole 122. The elastic composite 100 has the slightly-stretchable, opposite end areas 111 connected to the main body 121 and the highly-stretchable central area 110 rendered free, so that the highly-stretchable characteristics of the area 110 are not disturbed. The elastic composite 100 is connected at its opposite ends to the main body 121 to serve as a side panel of the diaper or training pants.

Examples of the present invention will now be described.

EXAMPLE 1

Manufacture of an Elongatable Non-woven Fabric 50 parts of polyester fibers (1/5 denier×35 mm) are mixed with 50 parts of polyester fibers (2 denier×51 mm). The mixture is introduced into a roller card to prepare a parallel carded web having a basis weight of 25 g/m².

The web has an orientation ratio MD/CD of 7. In other words, the strength of the web in the machine direction (MD) is seven times its strength in the cross direction (CD). The web is introduced over a porous suction cylinder provided with a dewatering zone while subjected to water-saturation, degassing and dewatering. The web is then passed at a running speed of 30 S m/min under three banks of water nozzles for water-entanglement.

| | |
|---|---|
| First nozzle: | 0.12 mm diameter × 0.4 mm pitch (distance between adjacent nozzles in a bank) water pressure 30 kg/cm² |
| Second nozzle: | 0.12 mm diameter × 0.4 mm pitch water pressure 50 kg/cm² |
| Third nozzle: | 0.20 mm diameter × 1.5 mm pitch water pressure 60 kg/cm² |

The entangled web as described above is dried and subsequently is subjected to heat treatment so that a web-form non-woven fabric having a basis weight of 30 g/m² is obtained.

Figure 18:
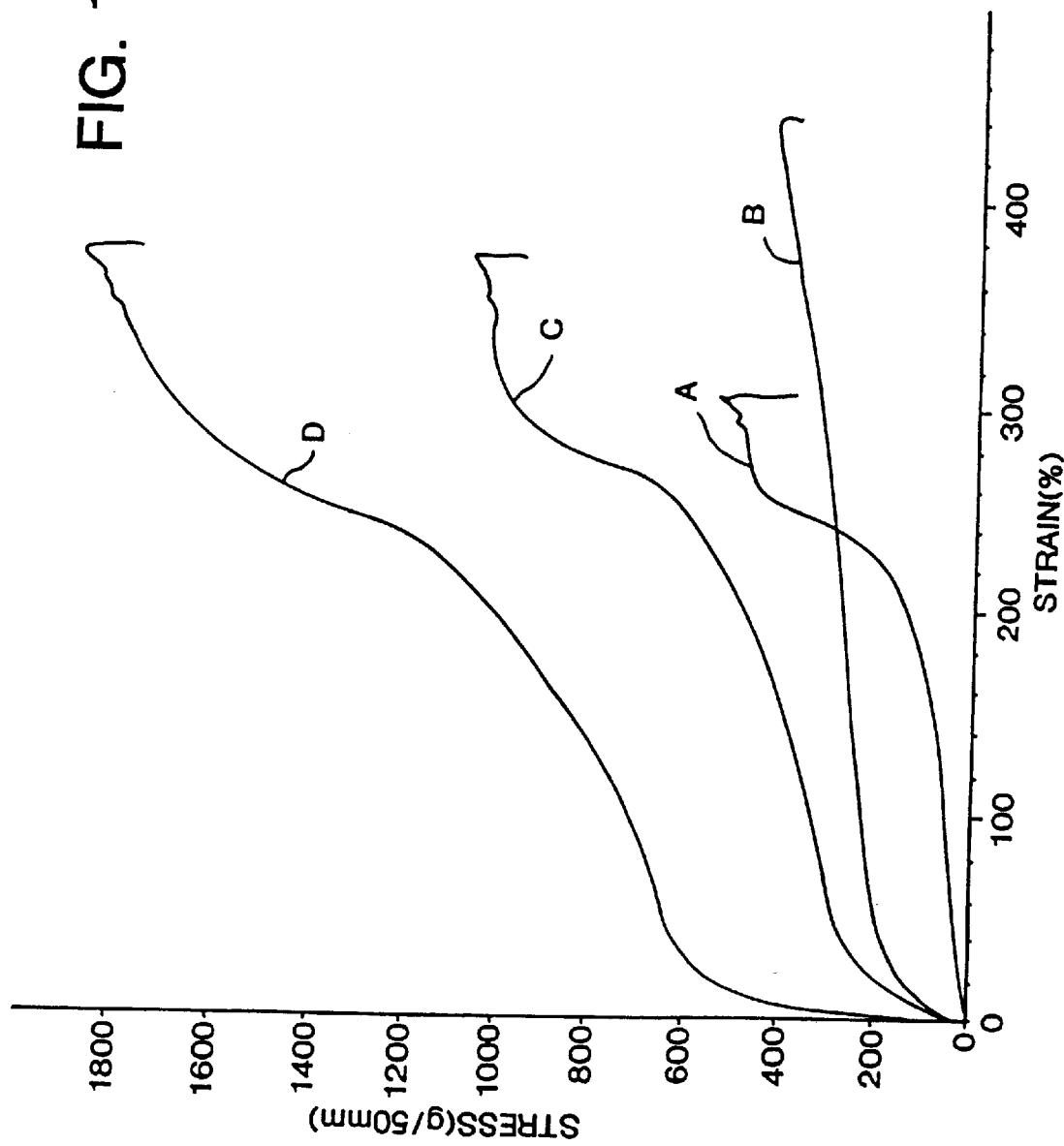
FIG. 18 is a graph showing S-S curves of the elastic composite as prepared in Example 1, the elastic sheet and the non-woven fabric as used in preparing the elastic composite of Example 1, respectively, when they are stretched in the CD.

An S-S curve of this non-woven fabric when stretched in CD is indicated at A in FIG. 18.

Preparation of an Elastic Sheet

A blend resin comprising EMA/EPDM (ethyl methyl acrylate/ethylene propylene diene terpolymer) polyolefin elastomer is extruded to form a film of 25 µm thick. An S-S curve of this elastic sheet when stretched in CD is indicated at B in FIG. 18.

One-sided Composite

The elastic sheet and the non-woven fabric as prepared above are superposed and laid over a 60-mesh PET net with the elastic sheet side facing toward the PET net. A heated roller having patterned annular grooves thereon is applied to the non-woven side while heated to 130° C. A flat or non-grooved roller is disposed beneath the PET net. The heated roller is pressed against the elastic sheet and fabric so that they are compressed against the flat roller at a line pressure of 10 kg/cm to form an elastic composite.

An S-S curve of the elastic composite thus produced when stretched in the CD is indicated at C in FIG. 18.

A three-cycle test which repeats the 150% stretch and release of the elastic composite provides results as shown FIG. 1. The measured recovery rate is 75%.

Two-sided Composite

Two sheets of the above elastic composite are placed upon each other so that their film sides face toward each other. A non-grooved surface heated roller heated up to 80° C. applies pressure to the sheets at a line pressure of 20 kg/cm and at a speed of 10 m/min so that a stable bonding condition is provided between the facing film sides of the two sheets. The securement regions in top and bottom sides are staggered from each other. An S-S curve of the resulting elastic composite is indicated by D in FIG. 18.

A three-cycle test which repeats the 150% stretch and release of this elastic composite provides results as shown in FIG. 2. The measured recovery rate is 75%.

EXAMPLE 2
One-sided Composite Comprising a SEBS-type Film and a Non-woven Fabric A composition primarily comprising a mixture of 75 parts SEBS and 25 parts EVA is extruded to prepare an elastic film of 25 μthick. Characteristically, this film can be easily bonded onto itself by compression at room temperature.

A slight amount (about 0.4 g/m$^2$) of rubber-type hotmelt adhesive is sprayed onto one surface of the film which then is bonded over its entire surface to a non-woven fabric similar to the one prepared in Example 1.

Two-sided Composite

Two sheets of the above elastic composite having the non-woven fabric secured on one side of the SEBS-type film are placed upon each other so that their respective film sides face toward each other. These two sheets are passed between a pair of non-grooved rolls at a temperature of about 40° C. and under a line of pressure of 20 kg/cm$^2$ to provide a two-sided composite which has the non-woven fabrics on its opposite sides and films stably secured to each other.

The one-sided and two-sided composites thus constructed show elastic recoveries similar to those of Example 1.

EXAMPLE 3

70 parts of polypropylene fibers (2 denier×30 mm) are mixed with 30 parts of polyester fibers (2 denier×57 mm). The mixture is introduced into a roller card to prepare a parallel carded web having a basis weight of 20 g/m$^2$. The web has a MD/CD ratio of 8.0.

The web is introduced over a net conveyor where it is placed upon a melt-blown non-woven fabric (manufactured by KURARAY Co., Ltd.) primarily constituted of SIS and having a basis weight of 40 g/m$^2$. The combined web and non-woven fabric are then introduced over a net provided with nozzles and a dewatering zone where they are subjected to a multi-stage hydro-entanglement treatment as detailed in the following Table 1.

TABLE 1

Figure 19A:
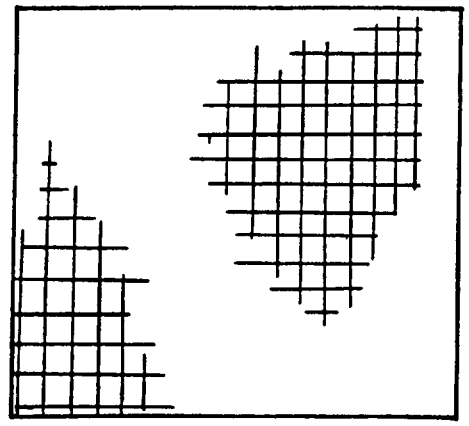
FIGS. 19A, 19B and 19C are explanatory plan views illustrating surface structures after the second-stage treatment of Example 3, after the third-stage treatment and after the fourth-stage treatment, respectively.
Figure 19B:
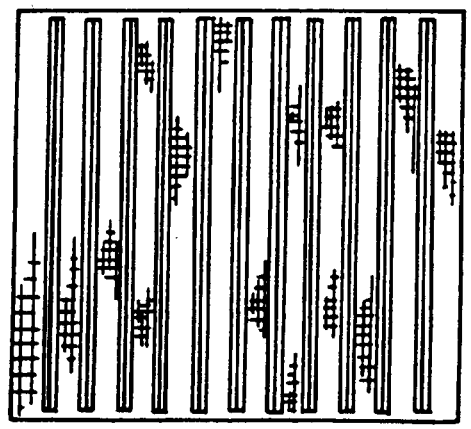
Figure 19C:
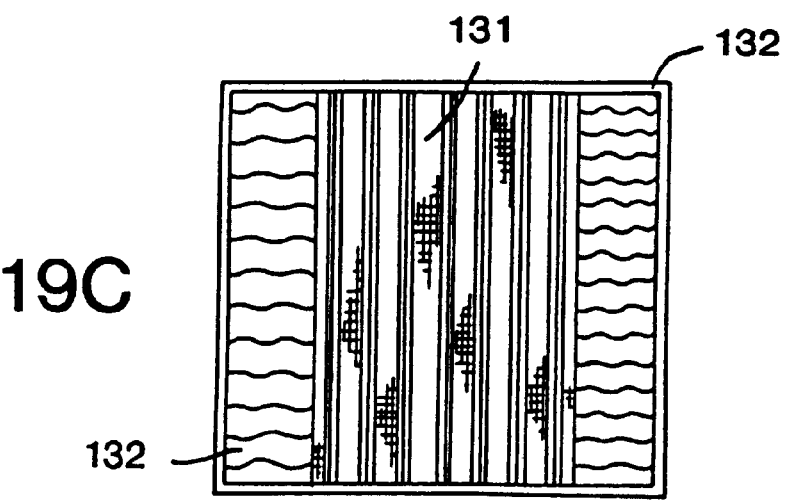

| Stage | Nozzle spec. | Pressure | Surface appearance of the obtained elastic composite |
|---|---|---|---|
| First stage (provisional stage) | 0.12 mmφ × 0.6 mm | 30 kg/cm$^2$ | — |
| Second stage (provisional stage) | 0.12 mmφ × 0.6 mm | 50 kg/cm$^2$ | Figure 19A |
| Third stage (partial entanglement) | 0.20 mmφ × 4.0 mm | 100 kg/cm$^2$ | Figure 19B |
| Fourth stage (partially inelasticizing treatment) | 0.15 mmφ × 0.6 mm | 80 kg/cm$^2$ | Figure 19C |

Figure 20:
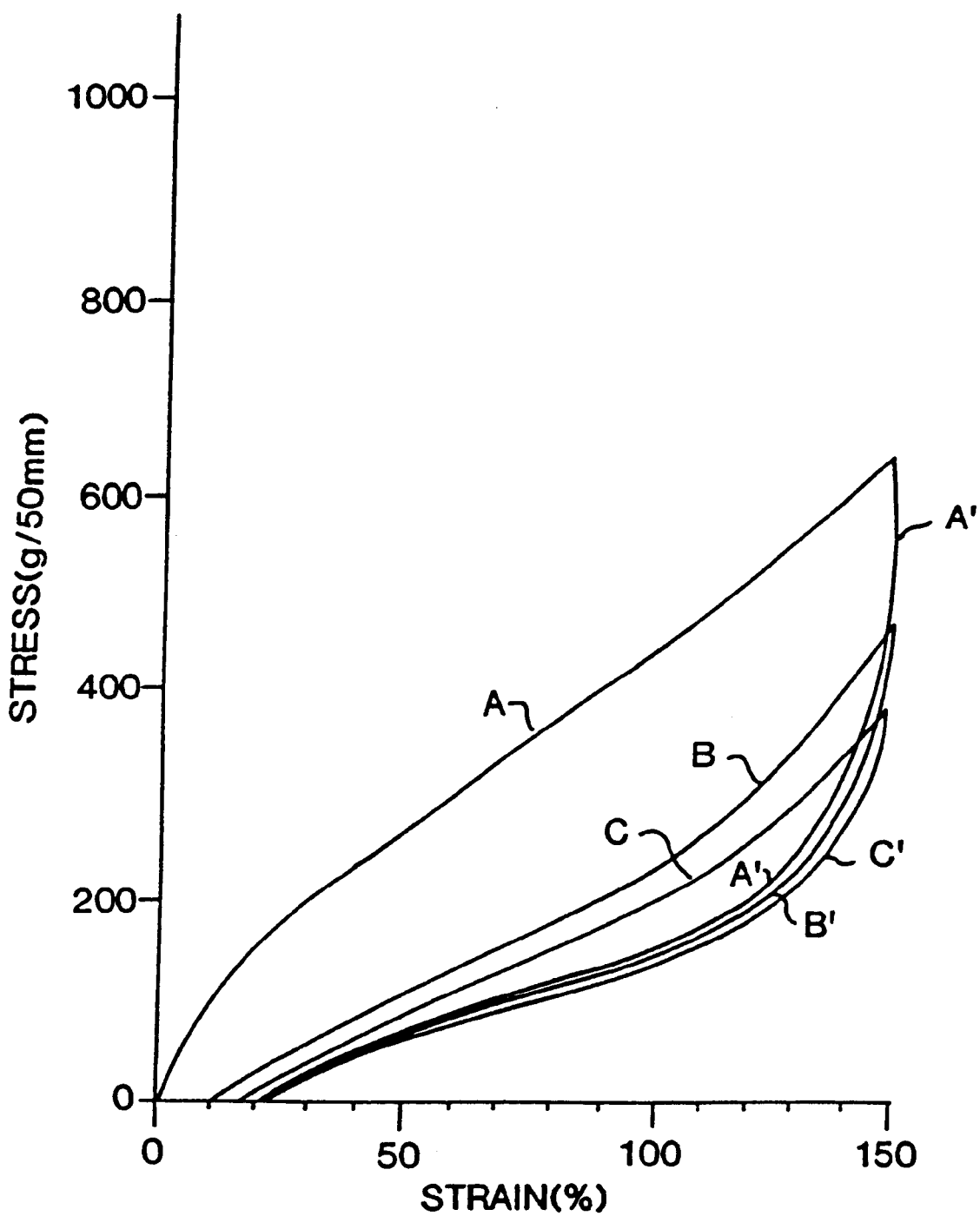
FIG. 20 is a graph showing results of a three-cycle test which repeats the 150% stretch and release of only the readily-stretchable portion of the elastic composite as prepared in Example 3.
Figure 21:
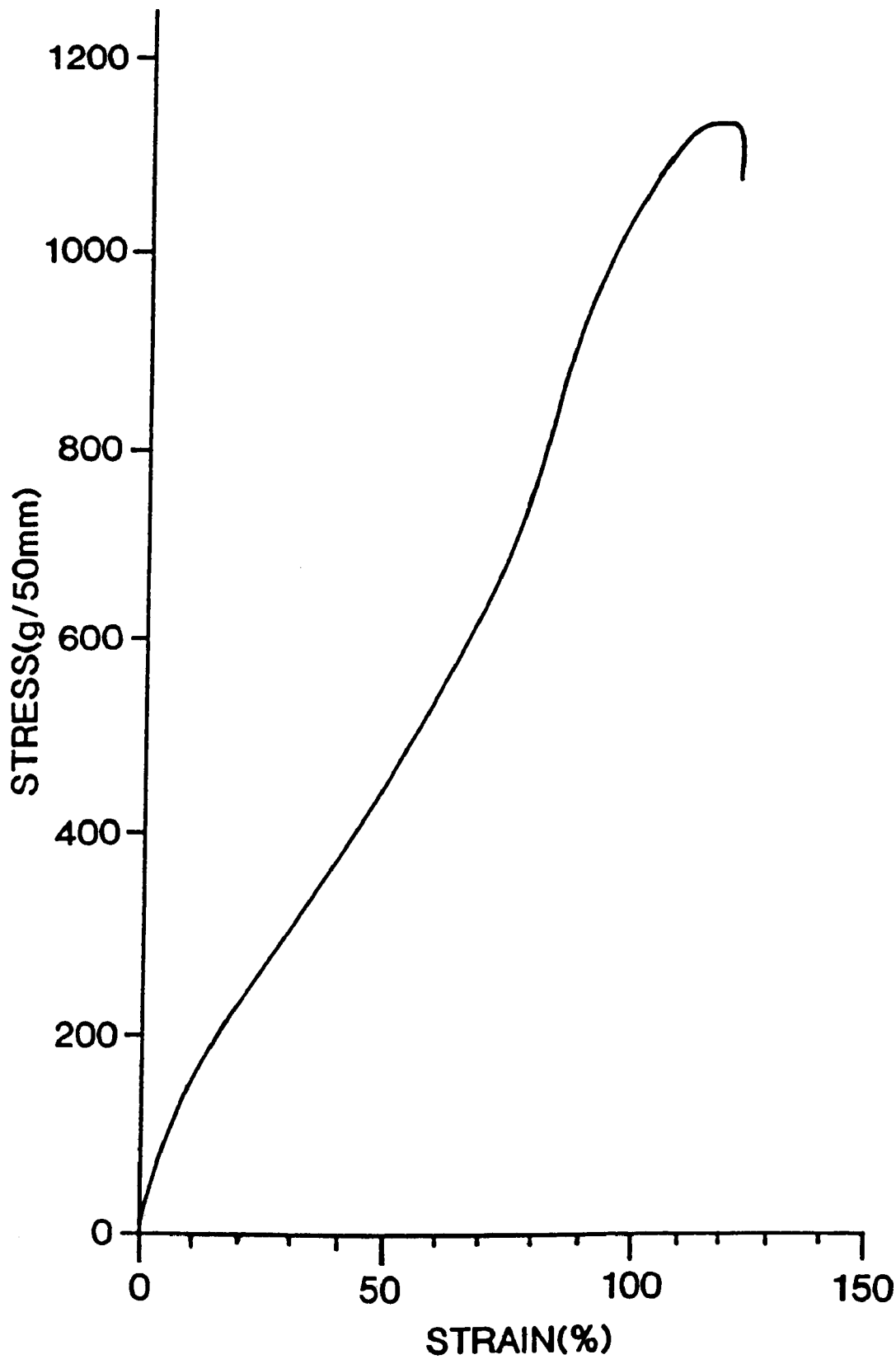
FIG. 21 is a graph showing results of a three-cycle test which repeats the 150% stretch and release of only the hardly-stretchable portion of the elastic composite as prepared in Example 3.

The surface structures of the composites obtained at various stages are shown in FIGS. 19A, 19B and 19C. The entangled elastic composite after the final stage has band-like readily-stretchable portions 131 and hardly-stretchable portions 132. A three-cycle test which repeats the 150% stretch and release of only the readily-stretchable portion 131 of the elastic composite provides results as shown in FIG. 20. The measured recovery rate is 70%. On the other hand, the hardly stretchable portion 132 hardly contracts elastically and provides a S-S curve as shown in FIG. 21. Its breaking point is shown to be 1.2 kg/50 mm.

As described above, the elastic composite in accordance with the present invention comprises a non-woven fabric which is potentially elongatable by higher than 100% in a specific direction, and an elastically recoverable elastic sheet. The non-woven fabric in its unelongated state is bonded to at least one surface of the unstretched elastic sheet through securement points to form the elastic composite which has recovery rate of higher than 60% after experiencing the three-repeated cycles of 150% stretch and release. Therefore, the elastic composite of the present invention provides excellent performance in elastic recovery and has a soft touch to the human skin. In particular, the elastic composite of the present invention can be advantageously utilized in elasticizing an article which is brought into direct contact with the human skin, such as a sleeve of a medical gown, or a waist or crotch portion of a sanitary article.

Although various embodiments of the invention have been described herein, it will be recognized that variations and modifications are possible without departing from the spirit of the invention as set out in the claims.

What is claimed is:

1. A stretch activated elastic composite comprising:
    a first non-woven fabric sheet adapted to be elongated by more than 100% in one direction; and
    a first elastically recoverable, elastic sheet;
    said first elastic sheet in its unstretched state being bonded at securement regions to one surface of said first non-woven fabric sheet in its unelongated state;
    said elastic composite before stress activation having, per unit width of 5 cm, when stretched in said one direction (1) a stress of lower than 1000 g at 30% stretch, (2) a stress of higher than 400 g at 100% stretch, (3) a breaking point of higher than 400 g, and (4) an elastic limit of higher than 200%,
    said elastic composite after stress activation by being stretched to an elongation of less than 200% having, per unit width of 5 cm, (1) a stress of lower than 500 g at 30% stretch and (2) a stress of higher than 100 g at 100% stretch, and
    said elastic composite after three repeated cycles of 150% stretching and relaxing having an elastic recovery rate of higher than 60% when measured based on JIS standards.

2. The elastic composite of claim 1, further comprising a second non-woven fabric sheet and wherein said first non-woven fabric sheet and second non-woven fabric sheet are bonded to opposite surfaces of said elastic sheet.

3. The elastic composite of claim 2, further comprising a second elastic sheet and wherein said first and second elastic sheets each have a first surface and an opposed second surface, said first non-woven fabric sheet bonded at said securement regions to the first surface of the first elastic sheet, said second non-woven fabric sheet bonded at second securement regions to the first surface of the second elastic sheet, and the second surfaces of said elastic sheets are bonded to each other.

4. The elastic composite of claim 3 wherein:
    said securement regions between said first non-woven fabric sheet and said first elastic sheet are offset from the second securement regions between said second non-woven fabric sheet and said second elastic sheet.

5. The elastic composite of claim 1 wherein
    said securement regions which bond said first elastic sheet and said non-woven fabric extends in an elongate band in a direction extending transversely of said one direction.

6. The elastic composite of claim 1 wherein
said securement regions which bond said first elastic sheet and said first non-woven fabric are arranged in rows which extend in a direction transversely of said one direction.

7. The elastic composite of claim 1 wherein
said first non-woven fabric comprises a fabric produced by water-entanglement and having a two-phase expandability at different stress levels.

8. The elastic composite of claim 7, wherein
said first non-woven fabric comprises a fabric whose elongation at a second phase takes place at an elongation rate of higher than 150%.

9. The elastic composite of claim 1 wherein
said first elastic sheet comprises heat-fusible material.

10. The elastic composite of claim 9, wherein said first elastic sheet and said first non-woven fabric are, in a specified area of the elastic composite, bonded to each other by heat compression above a temperature at which the first elastic sheet starts to melt but below a temperature at which the first non-woven fabric starts to melt to form a slightly-stretchable portion which is more resistant to stretching than the remaining portions.

11. The elastic composite of claim 10, wherein said slightly-stretchable portion is provided in a band-like manner.

12. The elastic composite of claim 9, wherein said first non-woven fabric consists of conjugated fibers which are easily fusible by heat.

13. A stretch-activated elastic composite comprising:
   a first non-woven fabric having a potential elongatability of higher than 100% in one direction; and
   a first elastically recoverable, elastic sheet;
   said first elastic sheet in its unstretched state being bonded to at least one surface of said first non-woven fabric in its unelongated state at securement points,
   said first elastic composite before stress activation having, per unit width of 5 cm, (1) a stress of lower than 800 g at 30% stretch, (2) a stress of higher than 600 g at 100% stretch, (3) a breaking point of higher than 400 g, and (4) an elastic limit of higher than 200%,
   said first elastic composite after stress activation by being stretched at a rate of lower than 200% having, per unit width of 5 cm, (1) a stress of lower than 300 g at 30% stretch and (2) a stress of higher than 200 g at 100% stretch, and
   said first elastic composite after three repeated cycles of 150% stretching and relaxing having an elastic recovery rate of higher than 60% when measured based on JIS standards.

14. A stretch-activated elastic composite comprising:
   a non-woven fabric sheet adapted to be elongated by more than 100% in one direction; and
   an elastic sheet having an elastic recovery rate of higher than 60% and an elastic limit of higher than 200%;
   said elastic sheet in its unstretched state being bonded at securement regions to one surface of said non-woven fabric sheet in its unelongated state;
   said elastic composite before stress activation having, per unit width of 5 cm, when stretched in said one direction (1) a stress of lower than 1000 g at 30% stretch, (2) a stress of higher than 400 g at 100% stretch, (3) a breaking point of higher than 400 g, and (4) an elastic limit of higher than 200%,
   said elastic composite after stress activation by being stretched to an elongation of less than 200% having, per unit width of 5 cm, (1) a stress of lower than 500 g at 30% stretch and (2) a stress of higher than 100 g at 100% stretch, and
   said elastic composite after three repeated cycles of 150% stretching and relaxing having an elastic recovery rate of higher than 60% when measured based on JIS standards.

* * * * *